US008604439B2

(12) United States Patent
Teshigawara et al.

(10) Patent No.: US 8,604,439 B2
(45) Date of Patent: Dec. 10, 2013

(54) NUCLEAR MEDICINE DIAGNOSIS APPARATUS

(75) Inventors: Manabu Teshigawara, Otawara (JP);
Takuzo Takayama, Otawara (JP);
Takaya Umehara, Kuki (JP); Tomoyasu Komori, Otawara (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 304 days.

(21) Appl. No.: 12/976,046

(22) Filed: Dec. 22, 2010

(65) Prior Publication Data
US 2011/0163238 A1   Jul. 7, 2011

(30) Foreign Application Priority Data
Jan. 5, 2010  (JP) .................... 2010-000737

(51) Int. Cl.
*G01T 1/164*   (2006.01)
(52) U.S. Cl.
USPC ................... 250/363.09; 250/363.03
(58) Field of Classification Search
USPC ........................ 250/363.09, 363.03
See application file for complete search history.

(56) References Cited

U.S. PATENT DOCUMENTS

| 2006/0065825 | A1 | 3/2006 | Ishitsu et al. | |
| 2007/0090297 | A1* | 4/2007 | Rutten et al. | 250/363.03 |
| 2007/0270693 | A1* | 11/2007 | Fiedler et al. | 600/436 |

FOREIGN PATENT DOCUMENTS

| JP | 2003-279652 | 10/2003 |
| WO | WO 2004/061479 A1 | 7/2004 |
| WO | WO 2006/018766 A2 | 2/2006 |
| WO | WO 2006/018766 A3 | 4/2009 |
| WO | WO 2009/040690 A2 | 4/2009 |
| WO | WO 2009/040690 A3 | 4/2009 |

OTHER PUBLICATIONS

Extended Search Report issued Apr. 5, 2013 in European Application No. 10196257.9.

* cited by examiner

*Primary Examiner* — Constantine Hannaher
(74) *Attorney, Agent, or Firm* — Oblon, Spivak, McClelland, Maier & Neustadt, L.L.P.

(57) ABSTRACT

According to one embodiment, a nuclear medicine diagnosis includes a light signal generating unit, photodetection unit, measurement unit, calculation unit, and storage unit. The light signal generating unit repeatedly generates light signals. The photodetection unit repeatedly generates first output signals corresponding to intensities of the light signals, repeatedly generates second output signals corresponding to intensities of gamma rays emitted from a subject. The measurement unit repeatedly measures light signal detection times and repeatedly measures gamma ray detection times. The calculation unit calculates a difference between a target gamma ray detection time and a target light signal detection time of the light signal detection times for each of the gamma ray detection times. The target light signal detection time is measured before the target gamma ray detection time. The storage unit stores the calculated difference in association with a target second output signal of the second output signals.

11 Claims, 10 Drawing Sheets

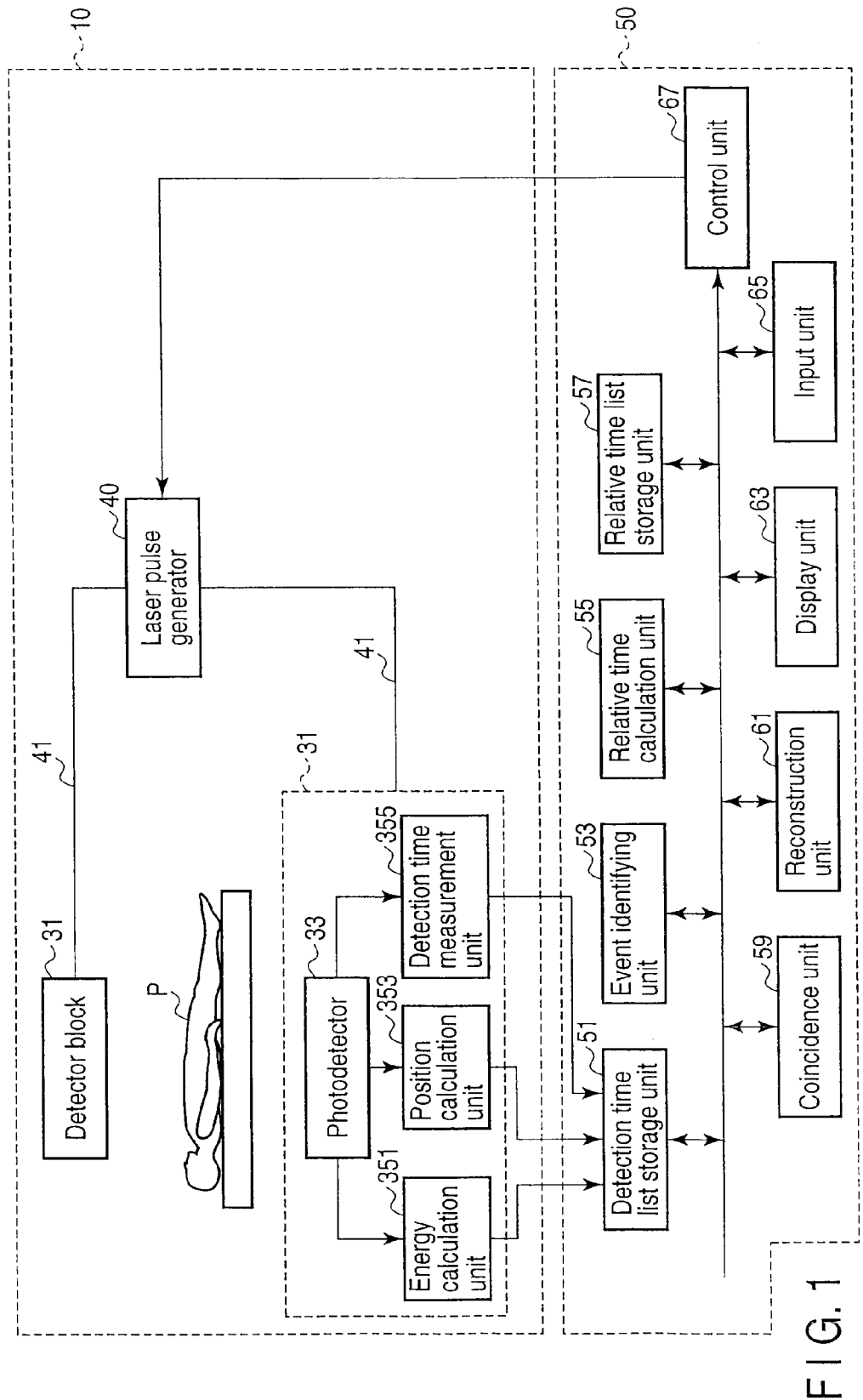
F I G. 1

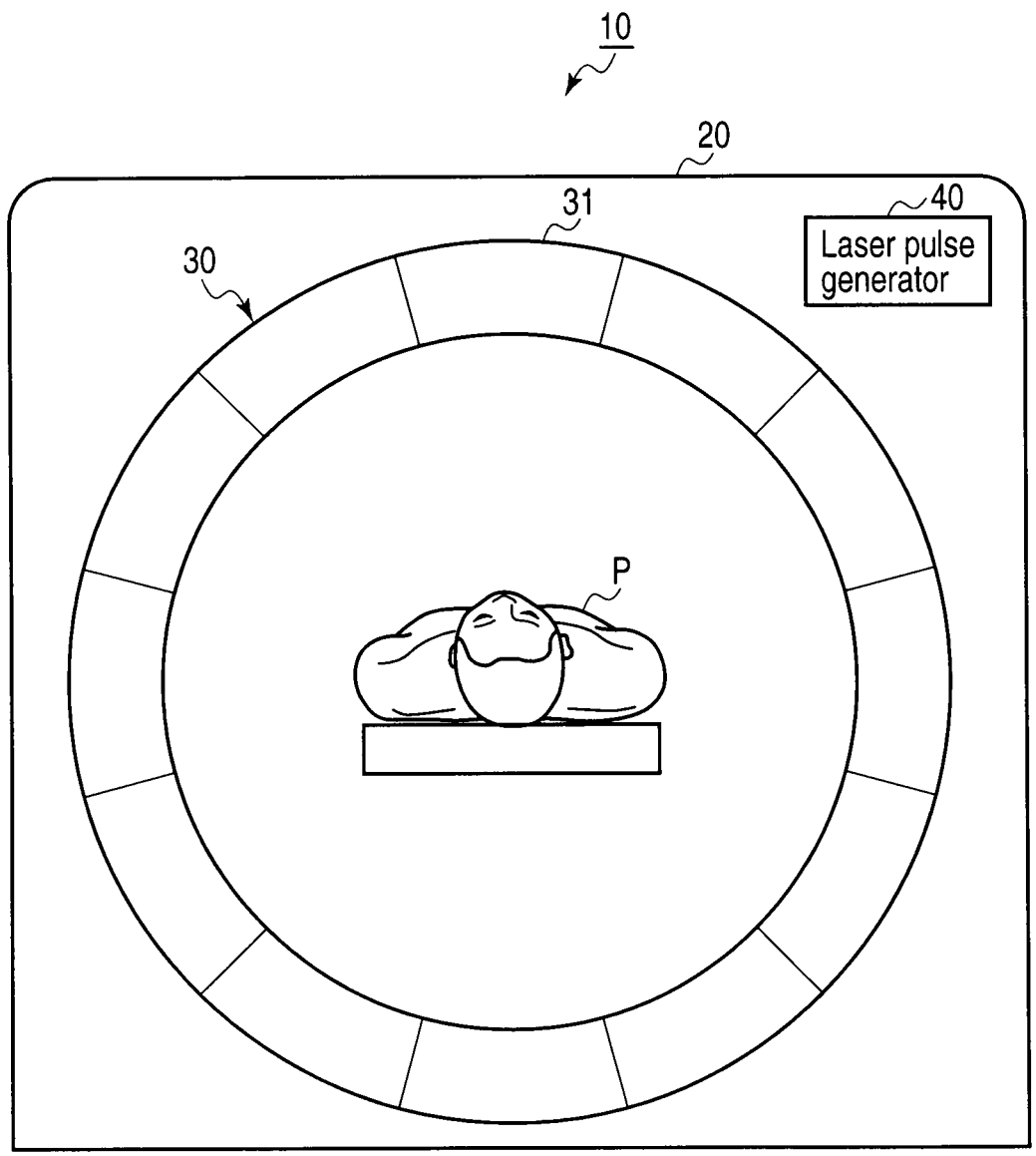
F I G. 2

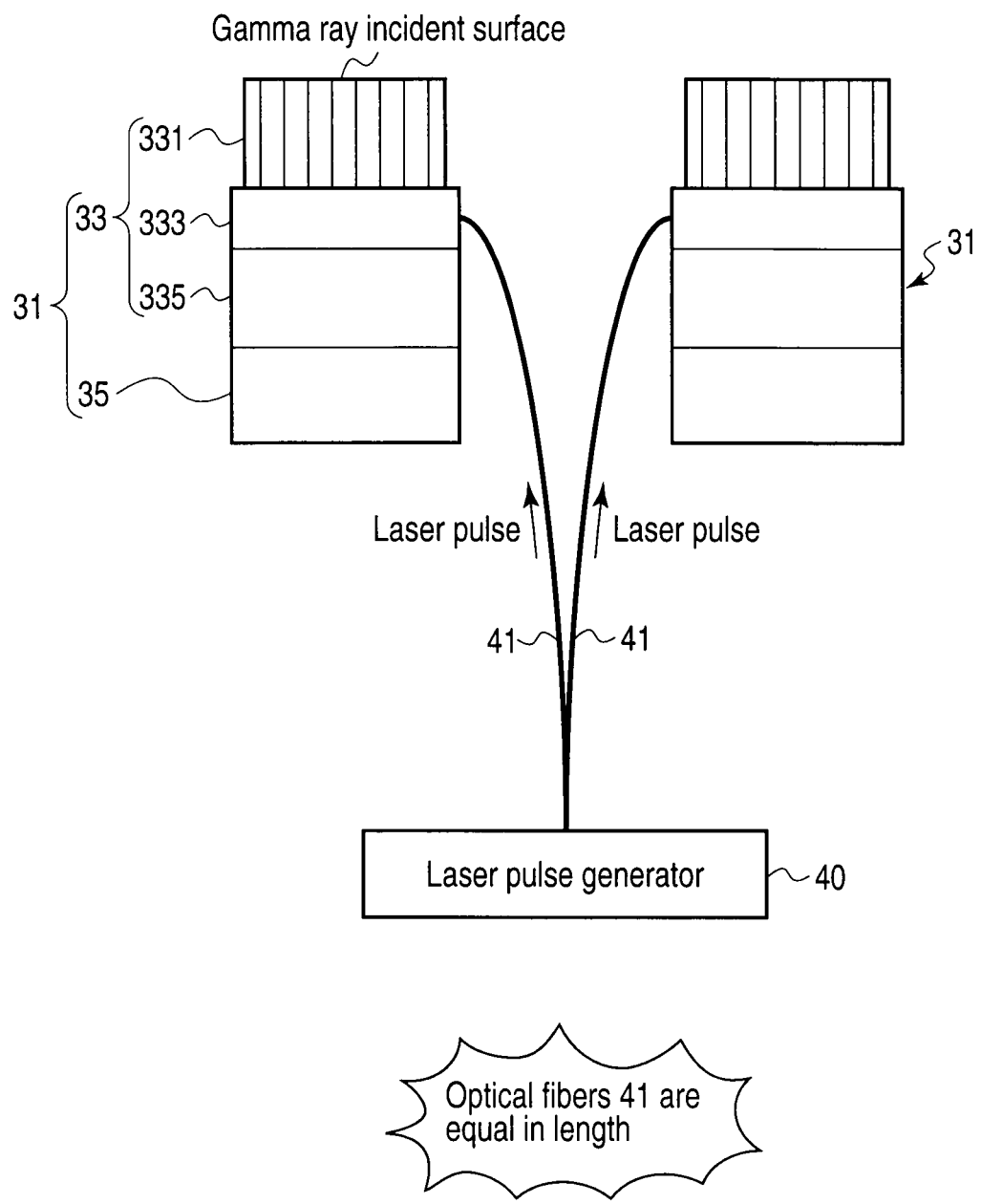
F I G. 3

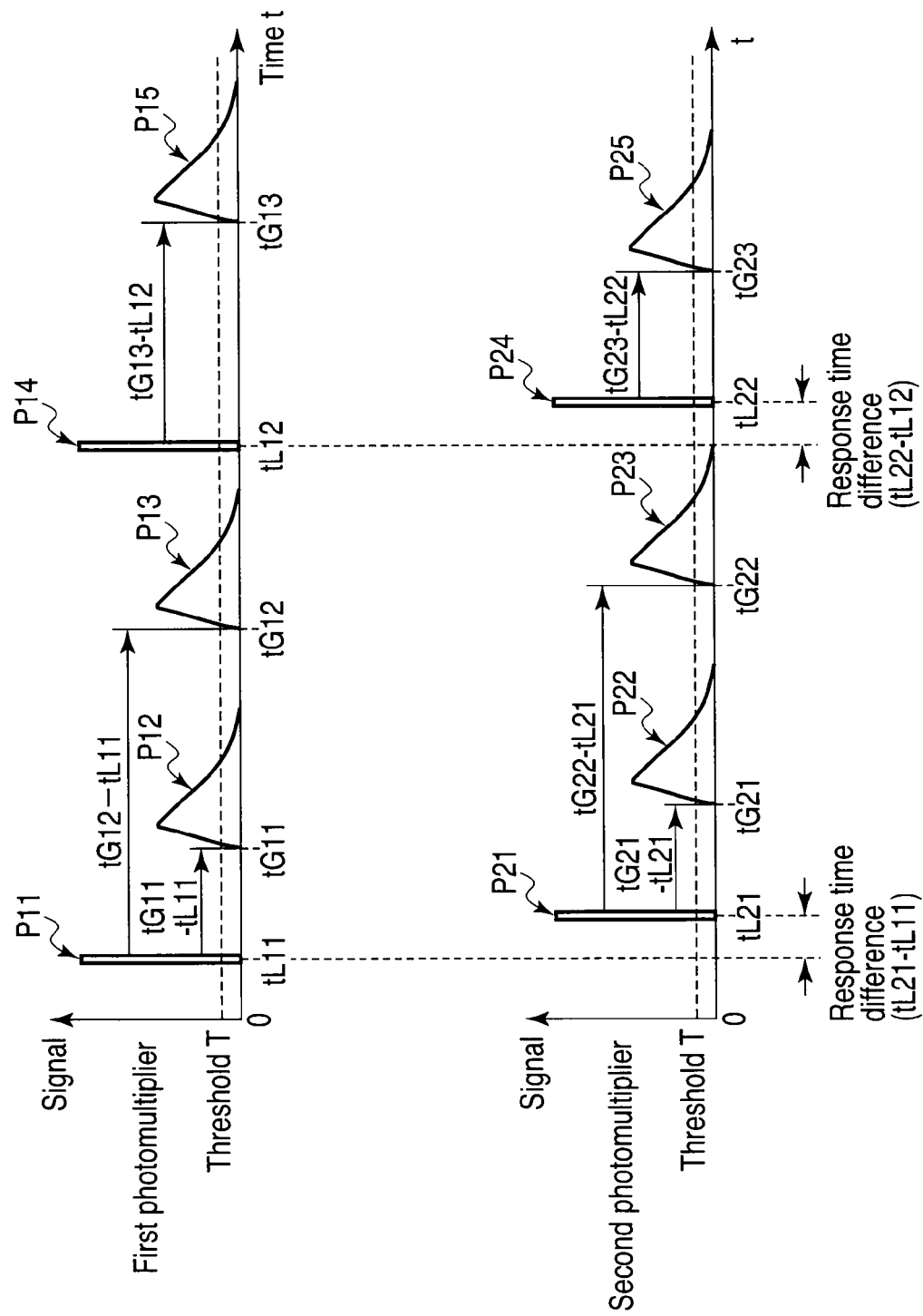
F I G. 6

Detection time list

| Event number | Photomultiplier | Scintillator | Detection time | Energy |
|---|---|---|---|---|
| 1 (Pseudo event) | PMT1 | SC3 | tL11 | EL1 |
| 2 (Pseudo event) | PMT2 | SC5 | tL21 | EL1 |
| 3 (Gamma event) | PMT1 | SC3 | tG11 | EG11 |
| 4 (Gamma event) | PMT2 | SC5 | tG21 | EG21 |
|  |  |  |  |  |

FIG. 8

Relative time list

| Event number | Photomultiplier | Scintillator | Relative time | Energy |
|---|---|---|---|---|
| 1 (Pseudo event) | PMT1 | SC3 | Reference | EL1 |
| 2 (Pseudo event) | PMT2 | SC5 | Reference | EL1 |
| 3 (Gamma event) | PMT1 | SC3 | tG11 − tL11 | EG11 |
| 4 (Gamma event) | PMT2 | SC5 | tG21 − tL21 | EG21 |
|  |  |  |  |  |

FIG. 9

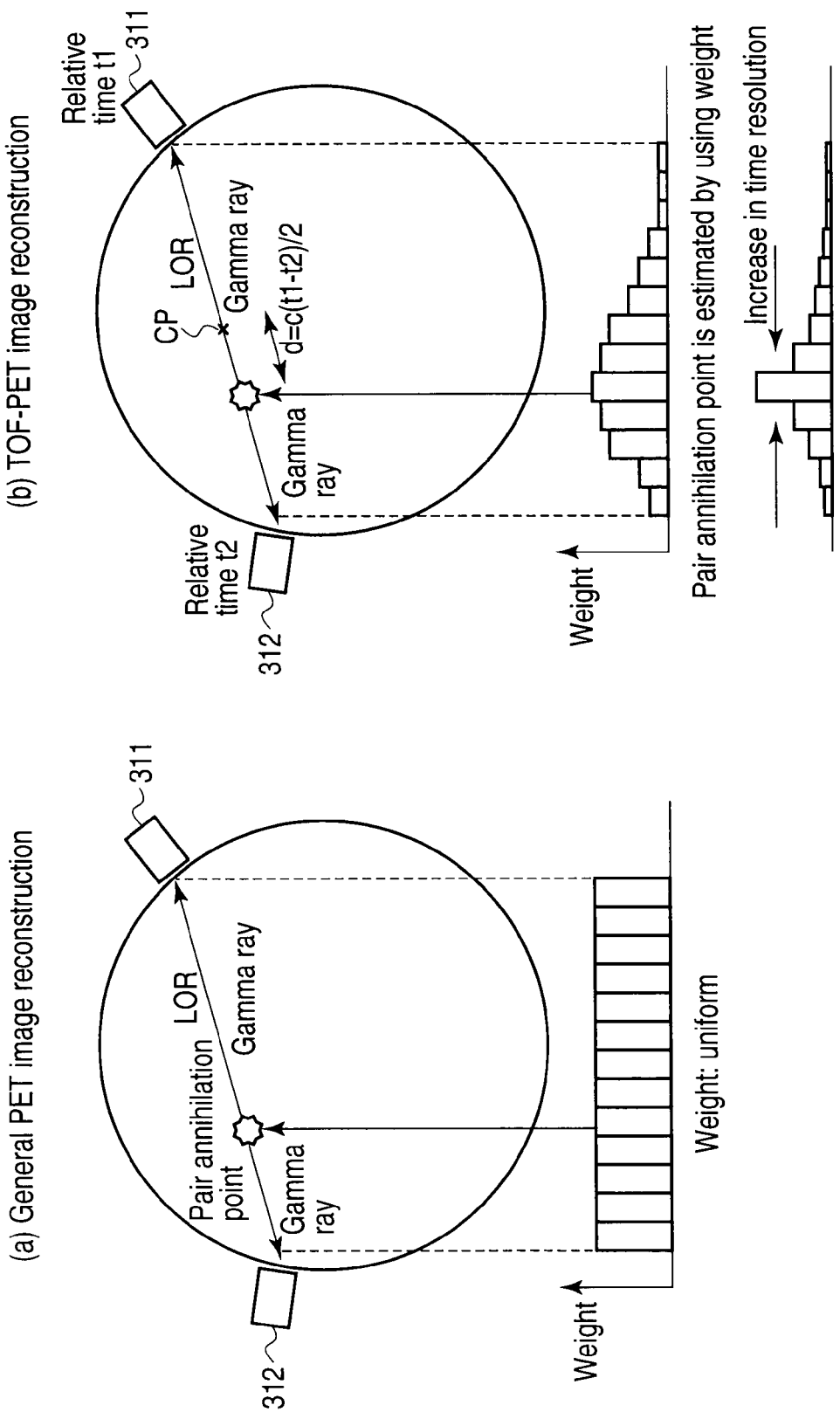
F I G. 10

NUCLEAR MEDICINE DIAGNOSIS APPARATUS

CROSS-REFERENCE TO RELATED APPLICATIONS

This application is based upon and claims the benefit of priority from Japanese Patent Application No. 2010-000737, filed Jan. 5, 2010; the entire contents of which are incorporated herein by reference.

FIELD

Embodiments described herein relate generally to a nuclear medicine diagnosis apparatus.

BACKGROUND

A nuclear medicine diagnosis apparatus performs, for example, PET (positron emission tomography) acquisition in the following manner. First of all, a medicine labeled with a radioactive isotope which emits positrons is administered to a subject. The nuclear medicine diagnosis apparatus repeatedly detects gamma rays emitted from the subject by using a plurality of photodetectors arranged around the subject in a ring form. The nuclear medicine diagnosis apparatus uses the detection times of gamma rays as time stamps, and identifies two gamma rays detected within a predetermined time frame. The two identified gamma rays are estimated to be generated from the same pair annihilation point. The nuclear medicine diagnosis apparatus estimates that the pair annihilation point exists on a line (LOR: line of response) connecting a pair of detectors by which the gamma rays have been simultaneously measured. To identify two gamma rays generated from the same pair annihilation point in this manner is called coincidence. The nuclear medicine diagnosis apparatus generates a PET image data based on output signals from the photodetectors associated with the LOR.

In order to specify the emission position of a gamma ray propagating at the velocity of light (about 300,000 km/s), it is necessary to assign the gamma event an accurate time stamp on the order of 10 ps. The nuclear medicine diagnosis apparatus is required to have a very high time resolution. This requires high-accuracy clock synchronization for all the photodetectors. This demands a very complicated and expensive mechanism. Furthermore, it is technically very difficult to implement clock synchronization on the order of 10 ps.

Each photodetector has an intrinsic response time (rise time). For this reason, the response time of each photodetector is measured in advance. The response times of the respective photodetectors are then corrected in accordance with the measurement results (calibration data) so as to equalize the response times of all the photodetectors. This correction is called timing calibration. The time resolution of the nuclear medicine diagnosis apparatus is improved by correcting the response times of all the photodetectors so as to equalize them. However, a very long time is required to obtain calibration data about all the photodetectors. In addition, the response time of each photodetector changes over time. For this reason, obtained calibration data is effective for only a short period of time. It is therefore necessary to frequently perform timing calibration for a long period of time. This imposes a very heavy load on the user.

BRIEF DESCRIPTION OF THE DRAWINGS

FIG. 1 is a block diagram showing the arrangement of a nuclear medicine diagnosis apparatus according to an embodiment;

FIG. 2 is a view showing the schematic arrangement of a gantry unit in FIG. 1;

FIG. 3 is a view showing the detailed structure of detector blocks and laser pulse generator in FIG. 1;

FIG. 6 is a graph showing electrical pulses repeatedly output from two different photomultipliers in FIG. 3;

FIG. 8 is a view showing an example of a detection time list stored in a detection time list storage unit in FIG. 1;

FIG. 9 is a view showing an example of a relative time list stored in a relative time list storage unit in FIG. 1;

FIG. 10 is a view showing the difference between a general PET image reconstruction method and a TOF-PET image reconstruction method, which are performed by a reconstruction unit in FIG. 1.

DETAILED DESCRIPTION

Figure 4:
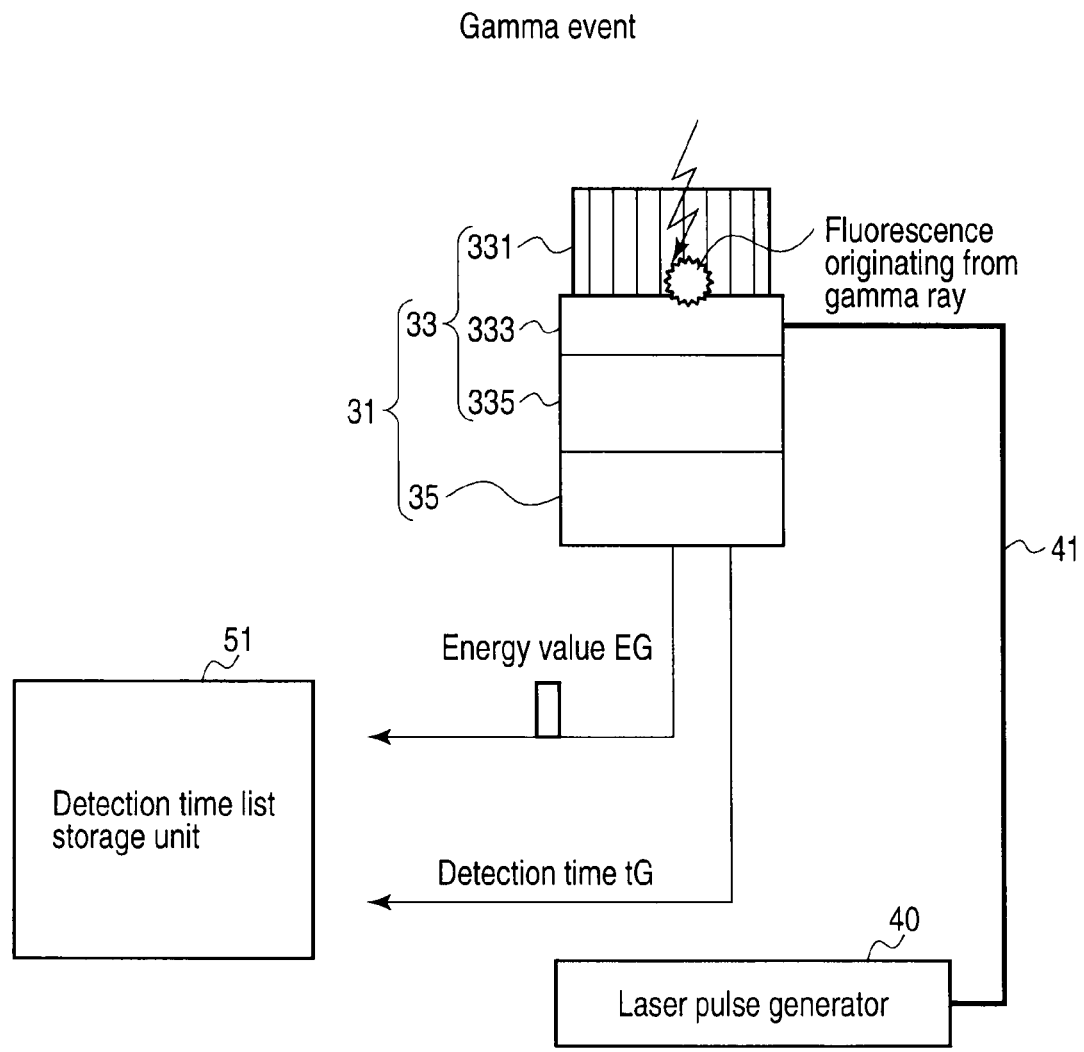
FIG. 4 is a view showing the input and outputs of the detector block in FIG. 1 at a gamma event.

In general, according to one embodiment, a nuclear medicine diagnosis includes a light signal generating unit, photodetection unit, measurement unit, calculation unit, and storage unit. The light signal generating unit repeatedly generates light signals. The photodetection unit repeatedly detects the generated light signals, repeatedly generates first output signals corresponding to intensities of the detected light signals, repeatedly detects gamma rays emitted from a subject, and repeatedly generates second output signals corresponding to intensities of the detected gamma rays. The measurement unit repeatedly measures light signal detection times of the light signals in the photodetection units and repeatedly measures gamma ray detection times of the gamma rays in the photodetection unit. The calculation unit calculates a difference between a target gamma ray detection time and a target light signal detection time of the light signal detection times for each of the gamma ray detection times. The target light signal detection time is measured before the target gamma ray detection time. The storage unit stores the calculated difference in association with a target second output signal of the second output signals.

The nuclear medicine diagnosis apparatus according to this embodiment will be described below with reference to the views of the accompanying drawing.

FIG. 1 is a block diagram showing the arrangement of the nuclear medicine diagnosis apparatus according to this embodiment. As shown in FIG. 1, the nuclear medicine diagnosis apparatus includes a gantry unit 10 and an image processing apparatus 50. FIG. 2 is a view showing the schematic arrangement of the gantry unit 10. As shown in FIG. 2, the gantry unit 10 includes a detector ring 30 and a laser pulse generator 40 inside a housing 20.

A top on which a subject P can be placed is inserted in the opening portion of the detector ring 30. The detector ring 30 includes a plurality of detector blocks 31 arranged around the long axis of the top in a circumferential form. Typically, a plurality of detector rings 30 are arranged along the long axis of the top.

The laser pulse generator 40 includes photoconductive paths (not shown) equal in number to the detector blocks 31 mounted inside the housing 20. Typically, the photoconductive paths are optical fibers. The laser pulse generator 40 repeatedly generates light signals, typically laser pulses, which can be detected by the detector blocks 31, at predetermined time intervals. The detector blocks 31 receive the generated laser pulses via the photoconductive paths.

FIG. 3 is a view showing the detailed structure of the detector blocks 31 and laser pulse generator 40. Although FIG. 3 (FIG. 1 as well) shows only the two detector blocks 31 for the sake of simplicity, more detector blocks 31 can be actually mounted inside the housing 20.

As shown in FIG. 3, each detector block 31 includes a photodetector 33 and a front end circuit 35.

The photodetector 33 detects light and generates an electrical signal corresponding to the intensity of the detected light. More specifically, the photodetector 33 detects a gamma ray emitted from an subject and generates an analog electrical signal (to be referred to as a gamma ray signal hereinafter) corresponding to the intensity of the detected gamma ray. The photodetector 33 also detects a laser pulse emitted from the laser pulse generator 40 and generates an analog electrical signal (to be referred to as a laser pulse signal hereinafter) corresponding to the intensity of the detected laser pulse. Note that "to detect light" will be referred to as "to generate events". In addition, "to detect gamma rays" will be referred to as "to generate gamma events", and "to detect laser pulses" will be referred to as "generate pseudo events".

More specifically, each photodetector 33 is obtained by joining a plurality of scintillators (crystals) 331, a light guide 333, and a photomultiplier 335 to each other.

Each scintillator 331 is made of a scintillator crystal formed in a rectangular parallelepiped shape. A scintillator crystal is a substance which generates fluorescence upon receiving gamma rays. The scintillators 331 are arrayed such that the gamma ray incident surfaces face the inside of the detector ring 30. For example, NaI (sodium iodide), BGO (bismuth germanate), or LSO (a substance obtained by adding a predetermined amount of cerium to lutetium silicate) is used for a scintillator crystal. One detector block 31 includes a plurality of scintillators 331 arrayed two-dimensionally. The light guide 333 is optically joined to the surfaces of the plurality of scintillators 331 on the opposite side to the gamma ray incident surfaces. The side surfaces of the respective scintillators 331 are coated with a reflective material. Fluorescence is guided to the light guide 333.

The light guide 333 is formed by a material having photoconductivity such as acrylic. The photomultiplier 335 is joined to the surface of the light guide 333 on the opposite side to the scintillator joint surface. An optical fiber 41 of the laser pulse generator 40 is optically joined to a side surface of the light guide 333. The light guide 333 guides fluorescence from the scintillators 331 or a laser pulse from the optical fiber to the photoelectric surface of the photomultiplier 335.

The laser pulse generator 40 includes optical fibers 41 equal in number to the detector blocks 31. All the detector blocks 31 and the laser pulse generator 40 in the housing 20 are joined to each other via the optical fibers 41. The laser pulse generator 40 repeatedly applies laser pulses to the light guide 333 of each detector block 31 via the corresponding optical fiber 41 at predetermined time intervals. Each laser pulse has a predetermined intensity. The duration of a laser pulse is sufficiently shorter than that of standard fluorescence (i.e., the duration of an electrical pulse originating from a gamma ray). All the optical fibers 41 have the same length. Typically, the lengths of the optical fibers are unified to the length of the optical fiber 41, of all the optical fibers 41 in the housing 20, which is joined to the light guide 333 physically farthest from the laser pulse generator 40. Unifying the lengths of all the optical fibers 41 in the housing 20 in this manner allows laser pulses to simultaneously strike all the light guides 333 in the housing 20.

The photomultiplier 335 is optically joined to the light guide 333 such that the photoelectric surface faces the light guide 333 side. The front end circuit 35 is joined to the surface of the photomultiplier 335 on the opposite side to the photoelectric surface. The photomultiplier 335 receives fluorescence from the scintillators 331 via the light guide 333, amplifies the received fluorescence, and generates a pulse-like electrical signal corresponding to the light amount of amplified fluorescence. The photomultiplier 335 also receives a laser pulse applied to the photomultiplier 335, amplifies the received laser pulse, and generates a pulse-like electrical signal corresponding to the light amount of the amplified laser pulse. In this manner, the photomultiplier 335 functions as an electrical signal generating unit. The front end circuit 35 receives the generated electric pulse. Note that this apparatus may include photodiodes functioning as electrical signal generating units in place of the photomultipliers 335.

The front end circuit 35 includes an energy calculation unit 351, a position calculation unit 353, and a detection time measurement unit 355 shown in FIG. 1.

The energy calculation unit 351 generates an electrical signal (energy signal) having an intensity corresponding to the energy value of light applied to the photodetector 33 based on an electrical signal from the photomultiplier 335. A detection time list storage unit 51 of the image processing apparatus 50 receives the energy value of the generated energy signal.

The position calculation unit 353 generates an electrical signal (position signal) having an intensity corresponding to the position coordinates to which light is applied, based on an electrical signal from the photomultiplier 335. Typically, position coordinates are those of the scintillators 331 which have generated light. Gamma rays actually strike the scintillators 331. Therefore, the position coordinates of a gamma ray calculated by the position calculation unit 353 are actually measured position coordinates. In practice, however, no laser pulse actually strikes the scintillators 331. Therefore, the position coordinates of a laser pulse calculated by the position calculation unit 353 are imaginary position coordinates. The detection time list storage unit 51 of the image processing apparatus 50 receives the generated position signal.

The image processing apparatus 50 internally processes a position signal in association with an energy value. The energy value with which a position signal is associated will be referred to as vent data hereinafter.

The detection time measurement unit 355 monitors the intensities of electrical signals supplied from the photomultiplier 335, and measures the time when light such as a laser pulse or gamma ray is detected by the photodetector. The detection time measurement unit 355 then generates detection time data indicting the detection time. The detection time list storage unit 51 of the image processing apparatus 50 receives the detection time data.

The image processing apparatus 50 includes the detection time list storage unit 51, an event identifying unit 53, a relative time calculation unit 55, a relative time list storage unit 57, a coincidence unit 59, a reconstruction unit 61, a display unit 63, an input unit 65, and a control unit 67.

The detection time list storage unit 51 stores the data of a detection time list. The detection time list is a list associating at least event data with detection time data for each event. On the detection time list, the detection time of each gamma event is used as a time stamp. The details of the detection time list will be described later.

The event identifying unit 53 refers to the detection time list stored in the detection time list storage unit 51 to identify, based on the energy value of each event, whether each event is a gamma event or pseudo event.

The relative time calculation unit 55 calculates the difference between the detection time of a gamma event and the detection time of a pseudo event. For example, the relative time calculation unit 55 calculates a difference by subtracting the detection time of a gamma event by the detection time of the corresponding pseudo event, i.e., the relative detection time of the gamma event relative to the detection time of the pseudo event. A gamma event and pseudo event as calculation targets are limited to events detected by the same photodetector 33. For example, the detection time of a gamma event as a calculation target is subtracted by the detection time of the pseudo event detected by the same photodetector 33 immediately before the detection time of the gamma event. The relative time list storage unit 57 receives the data concerning the calculated relative time.

The relative time list storage unit 57 stores the data of the relative time list. The relative time list is a list associating event data (projection data) concerning at least a gamma event with relative time data for each gamma event. On the relative time list, each relative time is used as the time stamp of a corresponding gamma event.

The coincidence unit 59 performs coincidence processing for gamma events by using relative times. More specifically, the coincidence unit 59 repeatedly identifies two gamma events falling within a predetermined time frame from the relative time list, and repeatedly identifies event data concerning the two gamma events. The two specified gamma events are estimated to originate from a pair of gamma rays generated from the same pair annihilation point. A line connecting a pair of photodetectors 33 which have detected a pair of gamma rays is called an LOR (line of interest). Repeating coincidence processing will identify event data concerning an LOR.

The reconstruction unit 61 reads out event data concerning the coincidence gamma events from the relative time list storage unit 57, and reconstructs the data of a PET image representing the density distribution of radioactive isotopes in the subject based on the readout event data.

The display unit 63 displays the PET image reconstructed by the reconstruction unit 61 on a display device. As a display device, a CRT display, liquid crystal display, organic EL display, plasma display, or the like can be properly used.

The input unit 65 accepts various kinds of commands and information inputs from the operator. More specifically, the input unit 65 inputs start and end instructions for PET acquisition and reconstruction processing via an input device, and inputs PET acquisition conditions and reconstruction conditions. As an input device, a keyboard, mouse, various kinds of buttons, a touch panel, and the like can be properly used.

The control unit 67 functions as the main unit of the nuclear medicine diagnosis apparatus. For example, the control unit 67 expands dedicated programs in its own memory, and performs PET acquisition and PET image reconstruction processing by controlling the respective units in accordance with the dedicated programs.

The nuclear medicine diagnosis apparatus according to this embodiment will be described in detail below.

The operation of the detector block 31 in each of events including a gamma event and a pseudo event will be described in detail first.

FIG. 4 is a view showing the input and outputs of the detector block 31 at a gamma event. As shown in FIG. 4, when a gamma ray strikes the scintillator 331, fluorescence is generated. The generated fluorescence reaches the photoelectric surface of the photomultiplier 335 via the light guide 333. The photomultiplier 335 converts the fluorescence into an electrical pulse and supplies it to the front end circuit 35. The front end circuit 35 then integrates the supplied electrical pulses for a predetermined period of time to generate an energy signal having an energy value EG originating from the detected gamma ray. The front end circuit 35 also monitors electrical pulses supplied via the photomultiplier 335 and measures detection time tG. The detection time list storage unit 51 receives the energy value of the energy signal EG and detection time data concerning the detection time tG.

Figure 5:
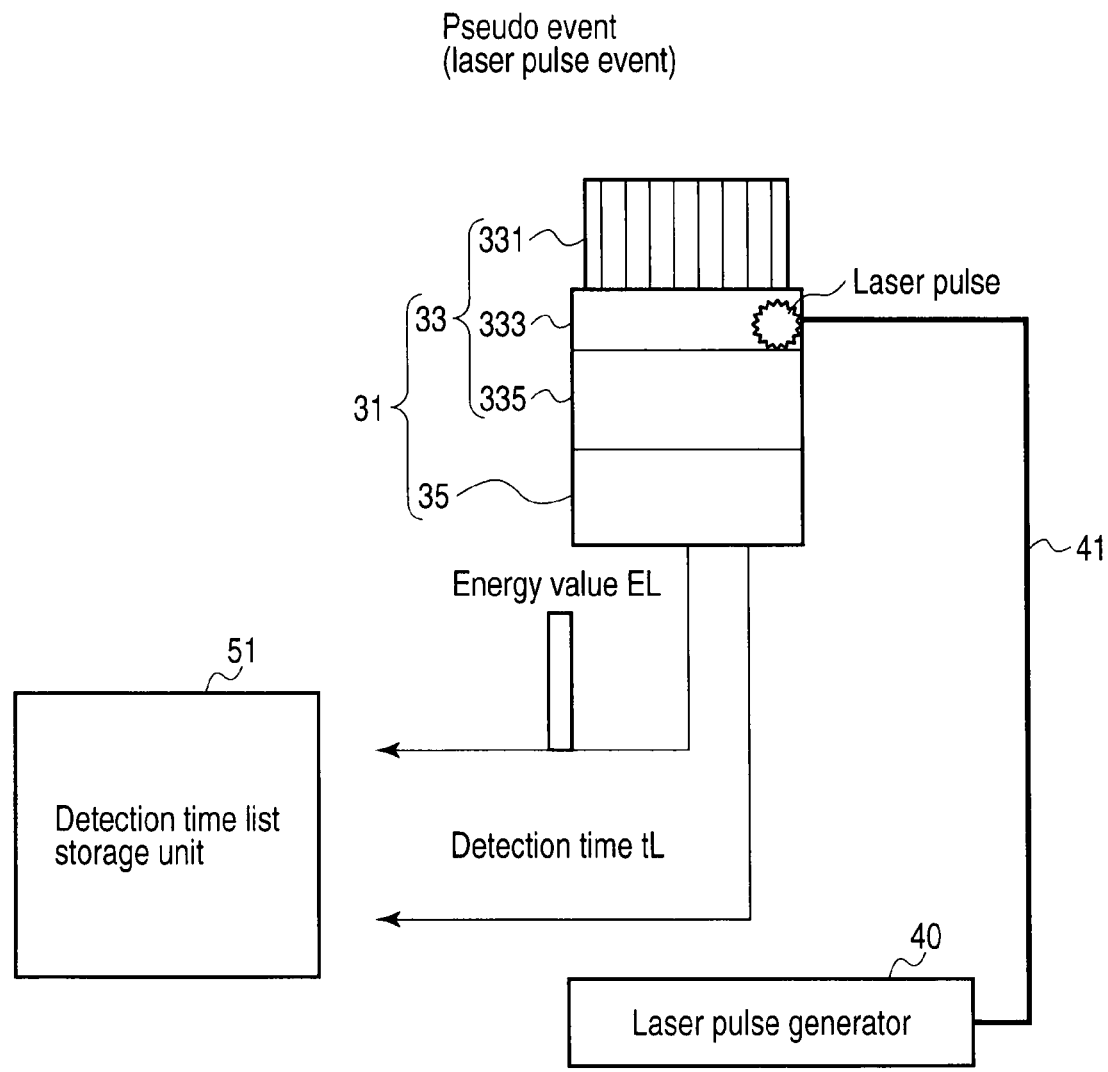
FIG. 5 is a view showing the input and outputs of the detector block in FIG. 1 at a pseudo event (laser pulse event)

FIG. 5 is a view showing the input and outputs of the detector block 31 at a pseudo event (laser pulse event). As shown in FIG. 5, a laser pulse generated by the laser pulse generator 40 strikes the light guide 333 via the optical fiber 41. The incident laser pulse reaches the photoelectric surface of the photomultiplier 335 via the light guide 333. The photomultiplier 335 converts the laser pulse into an electrical pulse, and supplies it to the front end circuit 35. The front end circuit 35 then integrates the supplied electrical pulses for a predetermined period of time to generate an energy signal having an energy value EL originating from the detected laser pulse. The front end circuit 35 also monitors electrical pulses supplied via the photomultiplier 335 and measures detection time tL. The detection time list storage unit 51 receives the energy value of the energy signal EL and detection time data concerning the detection time tL.

FIG. 6 is a graph showing electrical pulses repeatedly output from two different photomultipliers. The upper portion of FIG. 6 is a graph showing the relationship between an electrical pulse output from the first photomultiplier and a time t. The lower portion of FIG. 6 is a graph showing the relationship between an electrical pulse output from the second photomultiplier and the time t.

As shown in FIG. 6, assume that the first laser pulse, first gamma ray, second gamma ray, second laser pulse, and third gamma ray have sequentially struck the first and second photomultipliers each. This causes the first photomultiplier to sequentially generate an electrical pulse P11 concerning the first laser pulse, an electrical pulse P12 concerning the first gamma ray, an electrical pulse P13 concerning the second gamma ray, an electrical pulse P14 concerning the second laser pulse, and an electrical pulse P15 concerning the third gamma ray. Likewise, the second photomultiplier sequentially generates an electrical pulse P21 concerning the first laser pulse, an electrical pulse P22 concerning the first gamma ray, an electrical pulse P23 concerning the second gamma ray, an electrical pulse P24 concerning the second laser pulse, and an electrical pulse P25 concerning the third gamma ray.

The laser pulse generator 40 repeatedly applies laser pulses to the light guide at a rate of 1 ns at predetermined time intervals. In this case, the time interval between detection time tell of the first laser pulse and detection time tell of the second laser pulse is 1 ns. Note that the above arrangement causes the first and second laser pulses to respectively strike the first and second photomultipliers strictly at the same time on a real-time basis.

As described above, the energy calculation unit 351 implemented in the front end circuit calculates the energy value of each electrical pulse. More specifically, the energy calculation unit 351 monitors the energy values of electrical pulses and waits for an energy value to exceed a threshold T. When an energy value exceeds the threshold T, the energy calculation unit 351 starts to integrate the energy value. When the energy value becomes smaller than the threshold T, the energy calculation unit 351 finishes the integration. The resultant integral value is set as the energy value of the electrical pulse.

As described above, the detection time measurement unit 355 implemented in the front end circuit measures the detection time of each electrical pulse. More specifically, the detection time measurement unit 355 monitors the energy values of electrical pulses and waits for an energy value to exceed the predetermined trigger value ET. The detection time measurement unit 355 then measures the time when the energy value has exceeded the predetermined trigger value ET as the detection time of the event. Note that all the detection time measurement units 355 in the housing 20 need not be clock-synchronized. For example, with regard to an electrical pulse concerning the first gamma ray in the first photomultiplier, the detection time measurement unit 355 measures the time when the energy value has exceeded the trigger value ET as detection time tag. Each detection time measurement unit 355 therefore individually measures a detection time in accordance with clock pulses from the clock circuit which the unit has. Note that the information of a detection time may be the time defined by hour, minute, and second or the like or a relative time. For example, a relative time is defined by the time difference from a reference time such as a measurement start time.

As shown in FIG. 6, different photomultipliers will slightly differ in the response times to light due to some factors in the manufacture or aged deterioration even if they have the same product specifications. Along with such differences, the photomultipliers also differ in the rise times of electrical pulses from the instant at which fluorescence strikes the photoelectric surfaces of the photomultipliers. For example, the first photomultiplier detects the electrical pulse P11 originating from the first laser pulse at the time te11. The second photomultiplier detects the electrical pulse P21 originating from the first laser pulse at the time te11 later than the time te11. Obviously, therefore, there is a response time difference te11-te11 concerning the first laser pulse between the first and second photomultipliers. Similar response time differences occur concerning electrical pulses originating from other laser pulses and gamma rays.

In addition, even in the same photomultiplier, a response time to each electrical pulse sometimes slightly differs. However, the response times to a plurality of events detected by the same photomultiplier can be regarded as the same within a very short period of time like a laser pulse application interval. In other words, the response times to a pseudo event and gamma event can be regarded as the same within a very short period of time. That is, even if two photomultipliers differ in their response times, the time differences between the detection times of the gamma rays and the detection times of the pseudo events are the same on a real-time basis.

More specifically, as shown in FIG. 6, the time difference between the detection time tag of the first gamma ray and the detection time te11 of the first laser pulse in the first photomultiplier is given by tag-te11. The time difference between the detection time tag of the first gamma ray and the detection time te11 of the first laser pulse in the second photomultiplier is given by tag-te11. The time differences tag-te11 and tag-te11 are the same on a real-time basis. That is, if the time stamp of a gamma event represents the time difference (relative time) from a laser pulse, it is possible to cancel out the response time difference te11-te11 between the first and second photomultipliers in simultaneous measurement or the like.

Owing to the above reason, the nuclear medicine diagnosis apparatus according to this embodiment uses the relative detection time of a gamma event relative to the detection time of a pseudo event originating from a laser pulse as the time stamp of the gamma event.

Figure 7:
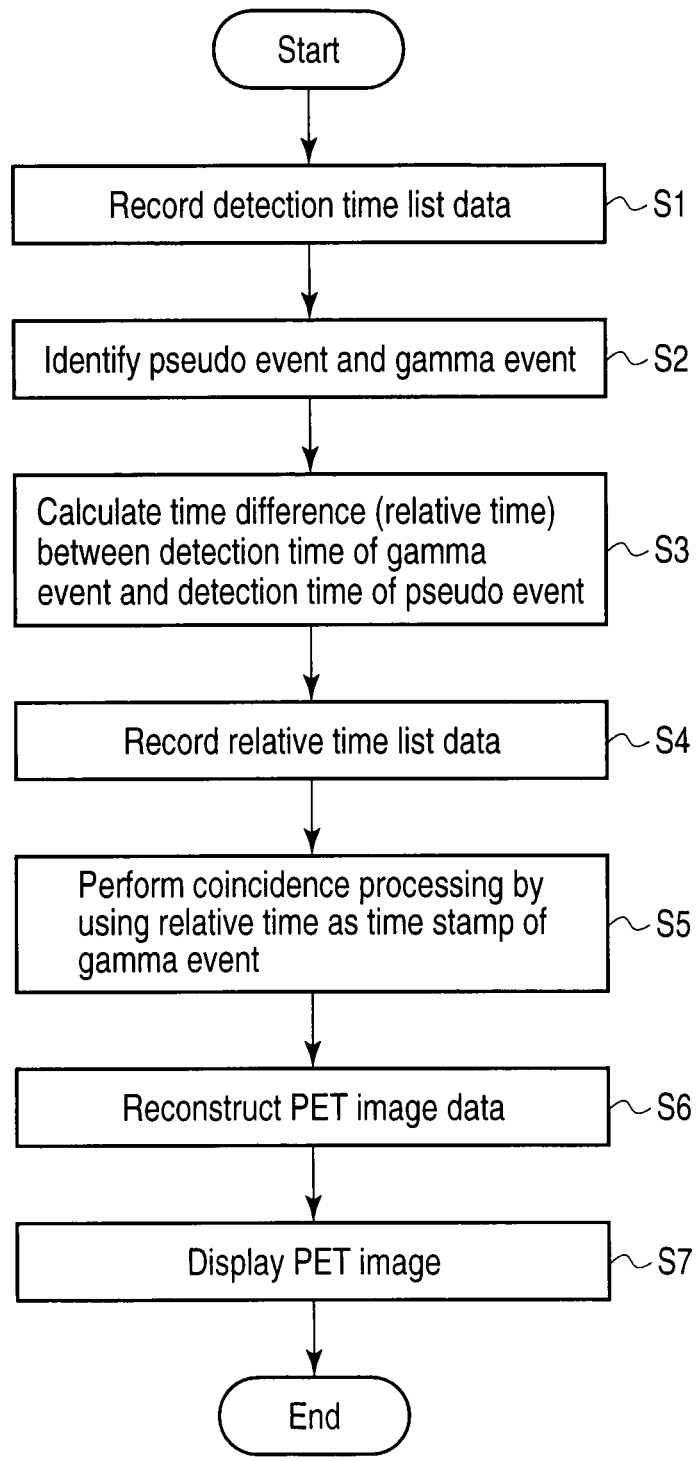
FIG. 7 is a flowchart showing a typical procedure of processing from PET acquisition to PET image display, which is executed under the control of a control unit in FIG. 1.

A typical example of the operation of the nuclear medicine diagnosis apparatus according to this embodiment will be described next with reference to FIG. 7. FIG. 7 is a flowchart showing a typical procedure of processing from PET acquisition to PET image display, which is executed under the control of the control unit 67.

First of all, a medicine labeled with a radioactive isotope which emits positrons is administered to a subject. For example, as radioactive isotopes, F18, O15, C11, N13, and the like are known. If, for example, fluorodeoxyglucose (FDG) labeled with F18 is used, a cancer is visualized in the form of a PET image. This is because cancers metabolize glucose more actively than normal cells. This makes it possible to detect a cancer. If a medicine exhibiting affinity to β-amyloid is labeled with C11, β-amyloid in the brain is visualized in the form of a PET image. This makes it possible to check a β-amyloid distribution in the brain.

When a medicine is administered to the subject and PET acquisition is prepared, the user inputs a start instruction for PET acquisition via the input unit 65. Upon receiving the start instruction, the control unit 67 starts PET acquisition by controlling the respective units. During PET acquisition, the control unit 67 controls the laser pulse generator 40 to simultaneously apply laser pulses to the light guides 333 of all the detector blocks 31 at predetermined time intervals.

In this state, the control unit 67 causes the detection time list storage unit 51 to record the detection time list data in real time during PET acquisition (step S1).

In step S1, the detection time list storage unit 51 sequentially records event data concerning pseudo events originating from laser pulses together with event data concerning general gamma events.

FIG. 8 is a view showing an example of a detection time list stored in the detection time list storage unit 51. As shown in FIG. 8, a detection time list includes items such as "event number", "photomultiplier number", "scintillator number", "detection time", and "energy". An event number is a number for identifying an event. A photomultiplier number is a number for identifying the photomultiplier 335 which has detected light concerning an event. A scintillator number is a number for identifying the scintillator 331 corresponding to the position coordinates calculated by the position calculation unit 353. A detection time is the detection time of an event measured by the detection time measurement unit 355. Energy is the energy value (the energy value of a gamma ray or laser pulse) calculated by the energy calculation unit 351. For example, the photomultiplier 335 with the number "PMT1" detects light corresponding to an event with the number "1" (pseudo event) at the detection time tL11, and calculates to find that the scintillator 331 with the number "SC3" has generated the light. This light has the energy value "EL1". Likewise, the photomultiplier 335 with the number "PMT2" detects light corresponding to an event with the number "4" (gamma event) at the detection time tG21, and calculates to find that the scintillator 331 with the number "SC5" has generated the light. This light has the energy value "EG21". In this manner, on the detection time list, a detection time is used as the time stamp of each event.

Note that it is possible to generate a detection time list for all the photomultipliers 335 or for each detector block 31.

Upon performing S1, the control unit 67 causes the event identifying unit 53 to perform identifying processing (step S2).

In step S2, the event identifying unit 53 identifies whether each event stored in the detection time list storage unit 51 is a pseudo event or gamma event. More specifically, the event identifying unit 53 determines whether the energy value associated with an identifying target event has the energy value EL corresponding to a laser pulse. Whether the energy value has the energy value EL is determined by determining whether the energy value of the identifying target event falls within a predetermined energy range including the energy value EL. Upon determining that the energy value of the identifying target event falls within the predetermined energy range, the event identifying unit 53 determines that the energy value has the energy value EL, and identifies the identifying target event as a pseudo event. The detection time list storage unit 51 stores, for example, codes representing pseudo events in association with, for example, the event numbers of the corresponding events. Upon determining that the energy value of the identifying target event does not fall within the predetermined energy range, the event identifying unit 53 determines that the energy value does not have the energy value EL, and identifies the identifying target event as a gamma event. The detection time list storage unit 51 stores codes representing gamma events in association with, for example, the event numbers of the corresponding events.

In step S2, the control unit 67 causes the relative time calculation unit 55 to calculate a relative time (step S3).

In step S3, the relative time calculation unit 55 calculates the time difference between the detection time of each gamma event stored in the detection time list storage unit 51 and the detection time of a corresponding pseudo event. More specifically, the relative time calculation unit 55 subtracts the detection time of the pseudo event from the detection time of the gamma event to calculate the relative detection time of the gamma event relative to the detection time of the pseudo event. The relative time calculation unit 55 calculates a relative time based on the detection time of a gamma event and the detection time of a pseudo event which are detected by the same photomultiplier 335. A calculation target pseudo event is limited to an event corresponding to a detection time immediately before the detection time of a calculation target gamma event. This makes it possible to reduce a deterioration in time stamp accuracy due to the response time differences between events in the same photomultiplier 335.

Calculation processing for a relative time will be described in detail with reference to the detection time list shown in FIG. 8. The following description will refer to a case in which a relative time is calculated for a gamma event with the event number "3". The photomultiplier 335 with the number "PMT1" detects the gamma event with the event number "3" at the detection time tG11. The relative time calculation unit 55 refers to the detection time list to specify the pseudo event detected by the photomultiplier 335 with the number "PMT1" at a time immediately before the detection time tG11. Assume that a pseudo event which satisfies this condition is the pseudo event with the event number "1". In this case, the relative time calculation unit 55 calculates the relative time tG11−tL11 by subtracting the detection time tL11 of the pseudo event with the event number "1" from the detection time tG11 of the gamma event with the event number "3".

Upon performing step S3, the control unit 67 causes the relative time list storage unit 57 to record the relative time list data (step S4).

In step S4, the relative time list storage unit 57 records, in the relative time list, the data of the relative time calculated by the relative time calculation unit 55 together with event data concerning the gamma event.

FIG. 9 is a view showing an example of the relative time list stored in the relative time list storage unit 57. As shown in FIG. 9, the relative time list includes items such as "event number", "photomultiplier number", "scintillator number", "relative time", and "energy". For example, the relative time of the gamma event with the event number "3" is given by tG11−tL11. In this manner, a relative time relative to a pseudo event is used as the time stamp of a gamma event on the relative time list. The time stamp based on the relative time is used for simultaneous measurement or the like.

In step S4, the control unit 67 causes the coincidence unit 59 to perform coincidence processing (step S5).

In step S5, the coincidence unit 59 performs coincidence processing for gamma events on the relative time list stored in the relative time list storage unit 57 by using relative times as the time stamps of the gamma events. More specifically, the coincidence unit 59 repeatedly identifies a pair of relative times included in a predetermined time frame among the plurality of relative times stored in the relative time list. The coincidence unit 59 then identifies a pair of event data associated with a pair of identified relative times in the relative time list. A pair of gamma events corresponding to a pair of relative times are estimated to be a pair of gamma events generated from the same pair annihilation point. A line connecting the pair of detector blocks 31 which have detected the pair of gamma events is an LOR. A code for identifying the LOR is associated with each of the event numbers of the pair of identified gamma events. This processing of identifying the pair of gamma events is performed for all the gamma events in the relative time list. Note that a time frame is set to, for example, about 6 ns to 18 ns. The coincidence unit 59 uses a relative time exhibiting a higher time resolution than a detection time as a time stamp without using a detection time as a time stamp as in the prior art. Therefore, the coincidence unit 59 can perform coincidence processing with higher accuracy and higher time resolution than the prior art.

Upon performing step S5, the control unit 67 causes the reconstruction unit 61 to perform reconstruction processing (step S6).

In step S6, the reconstruction unit 61 reads out the event data identified by the coincidence unit 59 from the relative time list storage unit 57, and reconstructs the data of a PET image based on the readout event data. The reconstruction methods which can be used include the general PET image reconstruction method which does not use the time difference between the time stamps of a pair of gamma events and the TOF (time of flight)-PET image reconstruction method which uses the time difference between the time stamps of a pair of gamma events.

FIG. 10 shows the difference between the general PET image reconstruction method and the TOF-PET image reconstruction method which are performed by the reconstruction unit 61. As shown in FIG. 10, the general PET image reconstruction method is a reconstruction method based on the assumption that "the existence probabilities of pair annihilation points at the respective points on an LOR are equal". Therefore, weights at the respective points on the LOR are uniform regardless of the distances from photodetectors. The reconstruction unit 61 generates the PET image data by performing reconstruction processing for event data by using weight set in this manner. When the reconstruction unit 61 uses the general PET image reconstruction method, since coincidence processing has been performed with a high time resolution as compared with the prior art by using relative times as time stamps, the image quality of a PET image is higher than that in the prior art.

In contrast, as shown in FIG. 10, the TOF-PET image reconstruction method is a method based on the assumption that "the existence probabilities of pair annihilation points at the respective points on an LOR change in accordance with the relative time differences between gamma events". Consequently, weights at the respective points on the LOR change in accordance with the distances from photodetectors. Weighting in the TOF-PET image reconstruction method will be described below. Assume that a first detector block 311 has detected a gamma event at relative time t1, and a first detector block 312 has detected a gamma event at relative time t2. In this case, a distance d from a central point CP of the LOR to a pair annihilation point is represented by equation (1). Note that c represents the velocity of light.

$$d=c(t1-t2)/2 \quad (1)$$

Equation (1) can calculate the position of a pair annihilation point on an LOR. When the position of a pair annihilation point is calculated, the reconstruction unit 61 sets a weight. The reconstruction unit 61 sets a weight so as to decrease its value as the distance from the pair annihilation point increases. The reconstruction unit 61 reconstructs the PET image data from the event data based on the weight set in this manner. This TOF-PET image reconstruction method can increase the S/N ratio as compared with the general PET image reconstruction method. In addition, the TOF-PET image reconstruction method according to this embodiment uses a relative time, as a time stamp, which increases the time resolution as compared with a detection time, instead of using a detection time as a time stamp as in the conventional TOF-PET image reconstruction method. Therefore, this TOF-PET image reconstruction method can calculate a pair annihilation point more accurately, i.e., with a higher time resolution, than the conventional TOF-PET image reconstruction method. This also allows the TOF-PET image reconstruction method to improve the image quality of a PET image as compared with the conventional method.

Upon performing step S6, the control unit 67 causes the display unit 63 to perform display processing (step S7).

In step S7, the display unit 63 displays the generated PET image on the display device. When the display device displays the PET image, the apparatus terminates the processing from PET acquisition to PET image display.

Note that this apparatus performs the processing in FIG. 7 concurrently with PET acquisition. However, this embodiment is not limited to this. For example, it is possible to perform the processing in steps S1 to S7 based on the data of a detection time list in a posteriori manner.

With the above arrangement, the nuclear medicine diagnosis apparatus according to this embodiment causes the laser pulse generator to generate pseudo events in the respective detector blocks simultaneously on a real-time basis during PET acquisition. The apparatus uses the time difference between the detection time of a gamma event and the time difference of a pseudo event as a time stamp. This new time stamp allows to cancel out the different response time differences between the respective detector blocks. The nuclear medicine diagnosis apparatus according to this embodiment can therefore obtain time stamps with higher accuracy and higher time resolution than the conventional apparatuses which have used the detection times of gamma events detected by detector blocks as time stamps. In addition, this apparatus need not establish clock synchronization in each detector block, which has been required for the conventional apparatuses. The nuclear medicine diagnosis apparatus according to this embodiment therefore need not include a mechanism for clock synchronization, and hence can be manufactured at a lower cost than the conventional apparatuses. Furthermore, the conventional apparatuses have measured the response time of each detector block, and incorporated a set of detector blocks having similar response times. The nuclear medicine diagnosis apparatus according to this embodiment can cancel out response times by using relative times as time stamps, and hence there is no need to measure the response times of detector blocks and implement a set of detector blocks having similar response times in the gantry unit 10. The nuclear medicine diagnosis apparatus according to this embodiment can also be configured to automatically perform timing calibration for detector blocks concurrently with PET acquisition. The nuclear medicine diagnosis apparatus according to the embodiment need not manually perform timing calibration before PET acquisition, which has been required in the prior art. This can save the user from manually performing timing calibration.

This embodiment can therefore provide a nuclear medicine diagnosis apparatus which can increase the time resolution while reducing the load on the user.

MODIFICATION

In the above embodiment, the optical fibers are joined to the light guides of the detector blocks. However, this embodiment is not limited to this. In a nuclear medicine diagnosis apparatus according to a modification, optical fibers are optically joined to scintillators.

Figure 11:
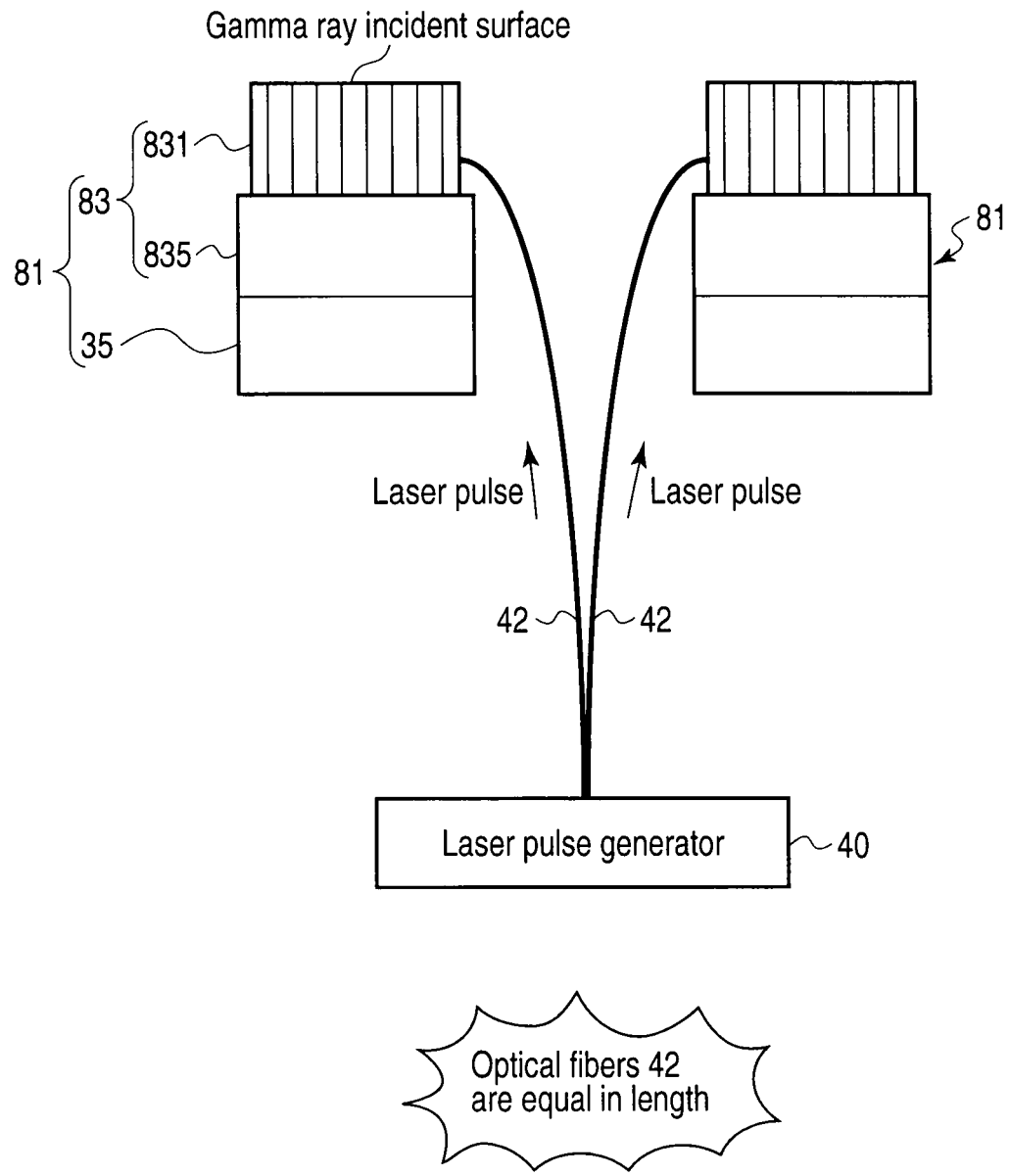
FIG. 11 is a view showing the detailed structure of detector blocks and laser pulse generator according to a modification of this embodiment.

FIG. 11 is a view showing the detailed structure of detector blocks 81 and laser pulse generator 40 according the modification. As shown in FIG. 11, each detector block 81 according to the modification includes a photodetector 83 and the front end circuit 35. The determination unit 81 has a structure having no light guide between a plurality of scintillators 831 and a photomultiplier 835. An optical fiber 42 is optically joined to a side surface of the scintillator of the plurality of scintillators 831 which is located at an end. The laser pulse generator 40 applies laser pulses to the scintillators 831 via the optical fiber 42. The laser pulses which have entered the scintillators 831 are guided to the photoelectric surface of the photomultiplier 835.

The photomultiplier 835 is optically joined to the plurality of scintillators 831 such that the photoelectric surface faces the scintillator 831 side. The front end circuit 35 is connected to the surface of the photomultiplier 835 on the opposite side to the photoelectric surface. The photomultiplier 835 receives fluorescence from the scintillators 831, amplifies the received fluorescence, and generates a pulse-like electrical signal corresponding to the light amount of the amplified fluorescence. The photomultiplier 835 also receives a laser pulse applied to the scintillator 831, amplifies the received laser pulse, and generates a pulse-like electrical signal corresponding to the light amount of the amplified laser pulse. The front end circuit 35 receives the generated electrical pulse. The subsequent processing is the same as that in this embodiment, and hence a description of the processing will be omitted.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnosis apparatus comprising:
a light signal generating unit configured to repeatedly generate light signals;
a photodetection unit configured to repeatedly detect the generated light signals, repeatedly generate first output signals corresponding to intensities of the detected light signals, repeatedly detect gamma rays emitted from a subject, and repeatedly generate second output signals corresponding to intensities of the detected gamma rays;
a measurement unit configured to repeatedly measure light signal detection times of the light signals in the photodetection units and repeatedly measure gamma ray detection times of the gamma rays in the photodetection unit;
a calculation unit configured to calculate a difference between a target gamma ray detection time and a target light signal detection time of the light signal detection times for each of the gamma ray detection times, the target light signal detection time being measured before the target gamma ray detection time; and
a storage unit configured to store the calculated difference in association with a target second output signal of the second output signals.

2. The apparatus according to claim 1, wherein the photodetection unit includes a plurality of photodetectors provided around a long axis of a top on which the subject is placed,
the light signal generating unit is joined to the plurality of photodetectors via a plurality of photoconductive paths, and
the plurality of photoconductive paths have substantially the same length.

3. The apparatus according to claim 2, wherein each of the plurality of photodetectors comprises a scintillator configured to generate fluorescence upon receiving light, an electrical signal generating unit configured to generate an electrical signal upon receiving fluorescence generated by the scintillator, and a light guide placed between the scintillator and the electrical signal generating unit, and
the light signal generating unit simultaneously applies the light signals to the respective light guides.

4. The apparatus according to claim 2, wherein each of the plurality of photodetectors comprises a scintillator configured to generate fluorescence upon receiving light and an electrical signal generating unit configured to generate an electrical signal upon receiving fluorescence generated by the scintillator, and
the light signal generating unit simultaneously applies the light signals to the respective scintillators.

5. The apparatus according to claim 2, wherein the light signal generating unit simultaneously applies a plurality of light signals to the plurality of photodetectors via the plurality of photoconductive paths.

6. The apparatus according to claim 2, wherein each of the plurality of photoconductive paths comprises an optical fiber.

7. The apparatus according to claim 2, wherein a target gamma ray and a target light signal measured by a same photodetector of the plurality of photodetectors, the target gamma ray being each of the gamma rays, the target light signal being each of the light signals.

8. The apparatus according to claim 7, wherein the target light signal comprises a light signal measured immediately before the target gamma ray detection time.

9. The apparatus according to claim 1, further comprising an identifying unit configured to identify a pair of second output signals, of the second output signals, which originate from a pair of annihilation gamma rays by using the difference as a time stamp.

10. The apparatus according to claim 1, further comprising an identifying unit configured to identify a pair of second output signals among the second output signals based on the difference and a predetermined time frame, the pair of second output signals originating from a pair of annihilation gamma rays.

11. The apparatus according to claim 10, further comprising a reconstruction unit configured to reconstruct image data concerning the subject based on the identified second output signals.

* * * * *